(12) United States Patent
Cerwin et al.

(10) Patent No.: US 8,573,391 B2
(45) Date of Patent: Nov. 5, 2013

(54) SUTURE PACKAGES PROVIDING UNCONSTRAINED DISPENSING OF SUTURES AND METHODS THEREFOR

(75) Inventors: Robert J. Cerwin, Pipersville, PA (US); Meredith McHugh Karow, Hatboro, PA (US); Raymond Parker, New Hope, PA (US)

(73) Assignee: Ethicon, Inc., Somerville, NJ (US)

( * ) Notice: Subject to any disclaimer, the term of this patent is extended or adjusted under 35 U.S.C. 154(b) by 264 days.

(21) Appl. No.: 12/719,592

(22) Filed: Mar. 8, 2010

(65) Prior Publication Data

US 2011/0215005 A1    Sep. 8, 2011

(51) Int. Cl.
*A61B 17/06* (2006.01)

(52) U.S. Cl.
USPC ......................................... 206/63.3

(58) Field of Classification Search
USPC ................. 206/63.3, 380, 438, 363
See application file for complete search history.

(56) References Cited

U.S. PATENT DOCUMENTS

| | | | | |
|---|---|---|---|---|
| 4,424,898 A | * | 1/1984 | Thyen et al. | 206/63.3 |
| 4,582,196 A | * | 4/1986 | Hughson et al. | 206/63.3 |
| 4,699,271 A | * | 10/1987 | Lincoln et al. | 206/63.3 |
| 4,961,498 A | * | 10/1990 | Kalinski et al. | 206/339 |
| 5,230,424 A | * | 7/1993 | Alpern et al. | 206/63.3 |
| 5,249,671 A | * | 10/1993 | Sinn | 206/63.3 |
| 5,472,081 A | * | 12/1995 | Kilgrow et al. | 206/63.3 |
| 5,494,154 A | * | 2/1996 | Ainsworth et al. | 206/63.3 |
| 5,533,611 A | * | 7/1996 | Bordighon et al. | 206/63.3 |
| 6,016,905 A | * | 1/2000 | Gemma et al. | 206/63.3 |
| 6,047,815 A | * | 4/2000 | Cerwin et al. | 206/63.3 |
| 6,076,659 A | * | 6/2000 | Baumgartner et al. | 206/63.3 |
| 6,098,796 A | * | 8/2000 | Januzeli et al. | 206/227 |
| 6,138,440 A | | 10/2000 | Gemma | |
| 7,520,382 B2 | | 4/2009 | Kennedy et al. | |
| 2006/0226031 A1 | | 10/2006 | Kennedy et al. | |
| 2007/0256945 A1 | | 11/2007 | Kennedy et al. | |
| 2009/0205987 A1 | | 8/2009 | Kennedy et al. | |

FOREIGN PATENT DOCUMENTS

EP    1214912 A2    6/2002

* cited by examiner

*Primary Examiner* — Jacob K Ackun

(57) ABSTRACT

A suture package includes a first part or base having an outer surface, an inner surface, and a plurality of openings extending between the outer and inner surfaces, and a second part or lid having an outer surface, an inner surface, and a plurality of posts projecting from the inner surface. The suture package has a closed configuration in which the inner surface of the lid opposes the inner surface of the base with distal ends of the posts engaging the inner surface of the base at locations that are offset from and adjacent the plurality of openings extending through the base. The package includes a hinge interconnecting the lid and the base for opening and closing the suture package. Suture winding posts on a fixture are passable through the base openings for winding at least one suture around the suture winding posts for positioning the at least one suture on the base.

17 Claims, 12 Drawing Sheets

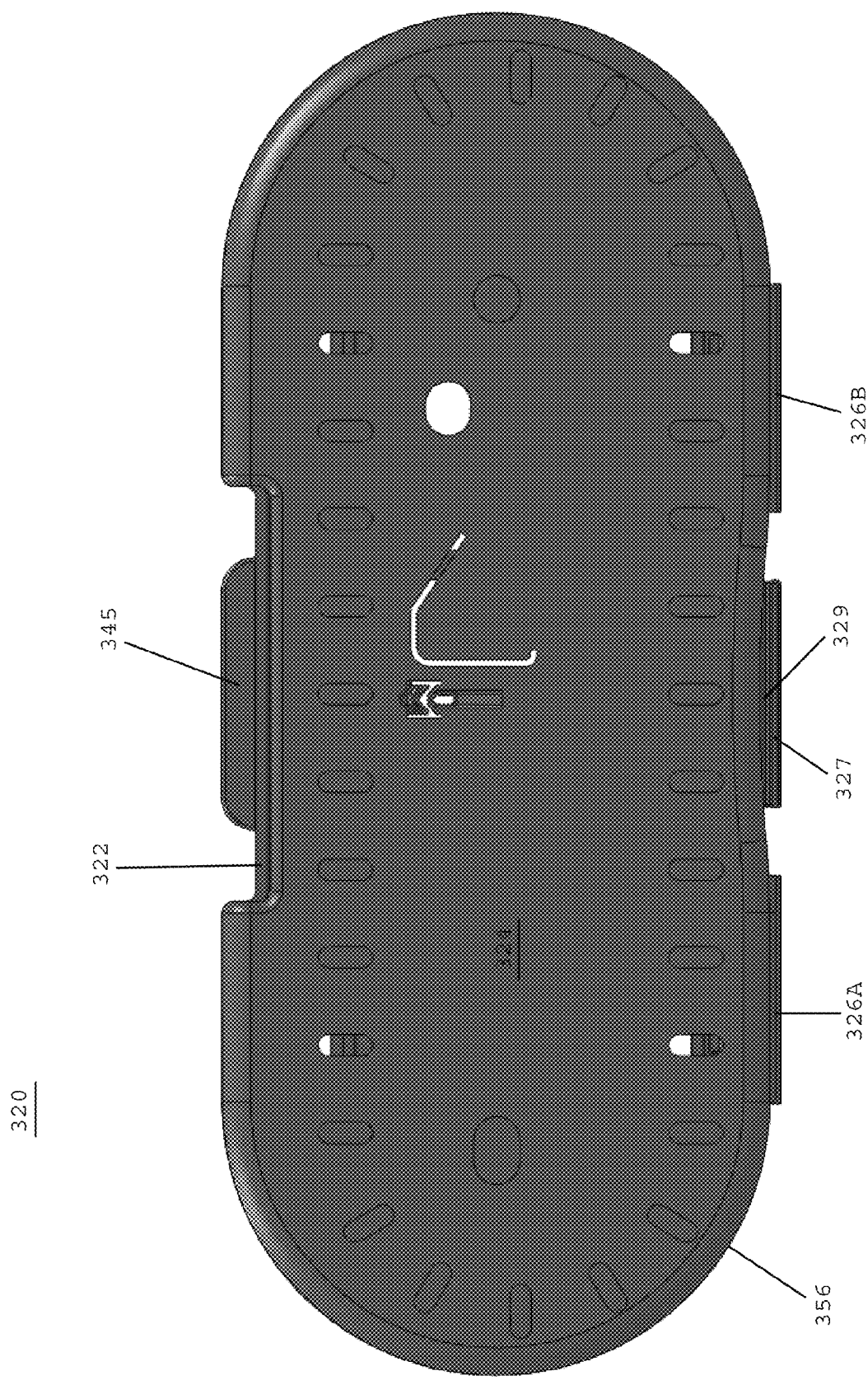

SUTURE PACKAGES PROVIDING UNCONSTRAINED DISPENSING OF SUTURES AND METHODS THEREFOR

BACKGROUND OF THE INVENTION

1. Field of the Invention

The present invention relates to surgical sutures, and more specifically relates to packages used for storing, shipping, and dispensing surgical sutures.

2. Description of the Related Art

Surgical sutures are used during surgical procedures for closing wounds and surgical openings. Sutures are frequently stored in sterile packages that are opened at a surgical site so that the suture may be removed from the package. A suture needle may be secured to one end of a suture for advancing the suture through tissue.

There have been a number of advances in suture packages. For example, U.S. Pat. No. 7,520,382 to Kennedy et al. discloses a suture package having a base member and a cover member. The base member includes an outer wall extending around an outer circumference thereof. The outer wall has a predetermined height that engages the cover member when the cover member is placed adjacent the base member. The package includes a partition structure that extends from a bottom surface of the cover member and defines at least once suture retaining area.

Covidien sells an absorbable wound closure device under the trademark V-LOC 180, which includes a tray that holds a surgical suture, and a flexible liner that covers the tray. The flexible liner cover may be pulled away from the tray for exposing the suture in the tray. The tray of the V-LOC 180 package includes a series of projections and flanges formed in the tray that are adapted to hold the suture within the tray during shipment and storage. Unfortunately, the projections and flanges in the tray have been found to constrain removal of the suture from the tray, which may have adverse consequences. For example, the suture may become entangled with the tray when being dispensed from the tray. Entanglement issues may be particularly prevalent for sutures having barbs, stops and/or loops.

In view of the above problems with conventional suture packages, there remains a need for improved suture packages that enable one or more sutures to be easily removed from the package for use during surgical procedures. There also remains a need for a suture package that does not have any constraining structure in the dispensing tray so that the suture may be freely removed from the tray without dragging the suture across surfaces, which may damage the suture or render the suture unusable.

SUMMARY OF THE INVENTION

In one embodiment, a suture package that provides for unconstrained dispensing of one or more surgical sutures preferably includes a first part or base having an outer surface, an inner surface, and a plurality of openings extending between the outer and inner surfaces of the base. The plurality of openings formed in the base may form one or more geometric patterns, such as oval, circular, square, rectangular, X-shaped patterns, etc. The pattern of the openings is preferably responsive to surgical requirements such as the length of suture required to be stored in the suture package. The suture package desirably includes a second part or lid having an outer surface, an inner surface, and a plurality of suture retaining posts projecting from the inner surface of the lid. The suture package desirably has an open configuration in which one or more sutures may be readily dispensed from the base, and a closed configuration in which the lid covers the base. In one embodiment, the base preferably includes a needle park adapted to secure a suture needle attached to a suture. In one embodiment, when the suture package is in the closed configuration, the inner surface of the lid preferably opposes the inner surface of the base with distal ends of the suture retaining posts engaging the inner surface of the base at locations that are offset from and adjacent the plurality of openings extending through the base.

In one embodiment, the base preferably includes an outer ridge projecting from the inner surface of the base, and the lid desirably includes an outer ridge projecting from the inner surface of the lid. In one embodiment, the opposing outer ridges are desirably adapted to engage one another when the suture package is closed. In one embodiment, the outer ridge of the base preferably defines an outer perimeter of the base, and the outer ridge of the lid preferably defines an outer perimeter of the lid. In one embodiment, the lid and the base have substantially the same size and shape so that the opposing outer ridges engage one another when the suture package is closed for sealing the outer perimeter of the package.

In one embodiment, the suture package preferably includes a hinge that interconnects the lid and the base for enabling the lid and base to move relative to one another for selectively opening and closing the suture package. In one embodiment, the hinge interconnects opposing trailing edges of the lid and the base so that the lid is able to swing relative to the base for opening and closing the package. In one embodiment, the suture package preferably includes a securing element such as a clasp that is engageable with at least one of the lid and the base for holding the suture package in the closed configuration. In one embodiment, the securing element is engaged for freeing the lid for being swung away from the base for opening the package. When the lid is swung back towards the base, the securing element may re-engage either the lid or the base for holding the package in a closed configuration.

In one embodiment, the lid desirably has the plurality of suture retaining posts integrally formed therewith. In one embodiment, proximal ends of the suture retaining posts are connected to the lid and distal ends are remote therefrom. In one embodiment, the suture retaining posts are desirably parallel with one another.

In one embodiment, the inner surface of the base of the suture package is preferably adapted to seat or receive at least one suture. The at least one suture is preferably wound over the base and held in position by the suture retaining posts when the package is closed.

In one embodiment, the suture package desirably includes a fixture that facilitates positioning, loading and/or winding one or more sutures over the inner surface of the base. In one embodiment, the fixture preferably includes a plurality of suture winding posts that project from a top surface of the fixture. In one embodiment, the suture winding posts are insertable through or passable through the plurality of openings provided in the base of the package. After the suture winding posts are passed through the plurality of openings in the base of the package, the upper ends of the suture winding posts are preferably disposed above the inner surface of the base. In one embodiment, at least one suture may be wound about the plurality of suture winding posts for providing at least one suture overlying the inner surface of the base. After the at least one suture has been wound around the suture winding posts, the suture winding posts may be retracted from the openings in the base of the package, leaving the wound suture material in place over the inner surface of the base.

In one embodiment, the fixture preferably includes a first region that is adapted to receive and/or seat the lid of the suture package and a second region that is adapted to seat and/or receive the base of the suture package. In one embodiment, the second region that receives the base preferably includes the plurality of suture winding posts projecting from the top surface thereof.

In one embodiment, the fixture preferably includes a plurality of suture winding post openings located in the second region of the fixture. The suture winding post openings are preferably accessible at the top surface of the fixture. The suture winding posts may be insertable into one or more of the suture winding post openings. In one embodiment, medical personnel may select a particular pattern for the suture winding posts and insert the suture winding posts into selected openings in the second region of the fixture to form that particular pattern. In one embodiment, the suture winding posts may be removed from the suture winding post openings when desired in order to create other preferred patterns for the suture winding posts. In one embodiment, the suture winding posts are permanently connected to the fixture for projecting from the top surface of the fixture.

In one embodiment, the first region of the fixture preferably includes a first depression formed in the top surface thereof that is preferably adapted to seat and receive the outer surface of the lid, and the second region of the fixture desirably includes a second depression formed in the top surface thereof that is preferably adapted to seat and receive the outer surface of the base. In one embodiment, the first and second depressions of the fixture have a size and shape that substantially matches the outer perimeters of the lid and the base for providing an additional methodology for aligning suture packages with the fixture.

In one embodiment, when the suture package is closed, each of the plurality of suture retaining posts that project from the inner surface of the lid preferably span a gap extending between the inner surface of the lid and the inner surface of the base. Although the present invention is not limited by any particular theory of operation, it is believed that providing suture retaining posts that span the entire gap between the inner surface of the lid and the inner surface of the base, when the package is closed, prevents suture material provided over the inner surface of the base from shifting beyond one of the retaining posts. Thus, the suture retaining posts define at least one "track" extending between the opposing inner surfaces of the lid and the base for constraining the suture material within the at least one "track" when the package is closed. When the package is opened by moving the lid away from the base, the suture retaining posts on the lid are pulled away from the inner surface of the base thereby eliminating the "track" and leaving the suture free to be removed from the package without constraints and without dragging the suture across any surfaces.

In one embodiment, the inner surface of the base preferably includes a plurality of recesses that are located adjacent the plurality of base openings. The recesses are preferably formed in the inner surface of the base. When the package is closed, the distal ends of the plurality of suture retaining posts projecting from the inner surface of the lid are preferably seated against and/or engage the recesses formed in the inner surface of the base.

In one embodiment, the lid and the base of a suture retaining package are preferably made of polymer materials such as plastic. In one embodiment, the suture package is an injected molded device.

In one embodiment, when the suture package is in the closed configuration, the suture retaining posts projecting from the inner surface of the lid preferably engage the inner surface of the base for defining at least one suture retaining "track" over the inner surface of the base that is adapted to constrain at least one suture between adjacent ones of the suture retaining posts. The "track" preferably remains in place as long as the suture package remains closed.

In one embodiment, a suture package preferably includes a base having an outer surface, an inner surface, and a plurality of openings extending between the outer and inner surfaces. The suture package desirably includes a lid having an outer surface, an inner surface, and a plurality of suture retaining posts projecting from the inner surface of the lid. The suture package preferably includes a hinge that interconnects the lid and the base for moving the suture package between an open configuration and a closed configuration in which the inner surface of the lid opposes the inner surface of the base with distal ends of the suture retaining posts engaging the inner surface of the base at locations that are offset from and adjacent the plurality of openings extending through the base. In one embodiment, the base preferably includes an outer ridge projecting from the inner surface of the base for defining a concave shaped base, and the lid includes an outer ridge projecting from the inner surface of the lid for defining a concave shaped lid. In one embodiment, the outer ridge of the lid is preferably adapted to engage the outer ridge of the base when the suture package is in the closed configuration for sealing the perimeter of the package. In one embodiment, the suture retaining posts are preferably integrally formed with the lid of the suture package.

In one embodiment, the suture package preferably includes a fixture for positioning at least one suture over the inner surface of the base. The fixture preferably includes a plurality of suture winding posts passable through the plurality of openings in the base when the base is positioned atop the fixture. In one embodiment, the fixture preferably includes a first region adapted to receive the lid and a second region adapted to receive the base. The second region preferably includes the plurality of suture winding posts projecting from a top surface thereof, which are adapted to pass through the base openings.

In one embodiment, a system for unconstrained dispensing of a suture includes a fixture having a top surface and a plurality of suture winding posts projecting from the top surface. The system desirably includes a suture package having a base and a lid positionable over the base for closing the suture package. The base desirably includes a plurality of openings passable over the suture winding posts so that the suture winding posts project above an inner surface of the base. In one embodiment, the system preferably includes at least one suture windable about the suture winding posts for positioning the at least one suture over the inner surface of the base. In one embodiment, the lid has suture retaining posts projecting from an inner surface thereof. The distal ends of the suture retaining posts preferably engage an inner surface of the base when the suture package is closed for constraining the at least one suture between adjacent suture retaining posts.

In one embodiment of the present invention, a suture package desirably enables a suture stored therein to be easily lifted out of the package when a lid is moved away from a base of the package. In one embodiment, the base of the suture package preferably includes a needle park in the center of the base and a plurality of openings that enable winding posts to be advanced therethrough to facilitate winding a suture on the base. After the suture is wound on the base, the winding posts are retracted from the openings in the base. In one embodiment, the lid of the suture package preferably includes suture retaining posts that are offset from the openings in the base.

The guide posts desirably form one or more "tracks" adapted to retain a previously positioned suture in position on a base during shipping and storage. When medical personnel open the suture package to remove the suture, the guide posts in the lid are desirably pulled away from the base with the lid, thereby eliminating the one or more "tracks" and enabling unconstrained dispensing of one or more sutures from the suture package without dragging the one or more sutures across any surfaces, flanges, or corners. The position of the suture may be set in place using various techniques. In one embodiment, after a suture is positioned over the inner surface of a base, the position of the suture may be set in-place by exposing the suture to heat.

These and other preferred embodiments of the present invention will be described in more detail below.

BRIEF DESCRIPTION OF THE DRAWING

FIGS. 2G-1 shows a magnified view of the step shown in FIG. 2G.

FIG. 5 shows a bottom view of a suture package used for storing, shipping, and dispensing a surgical suture, in accordance with one embodiment of the present invention.

DETAILED DESCRIPTION

Figure 1A:
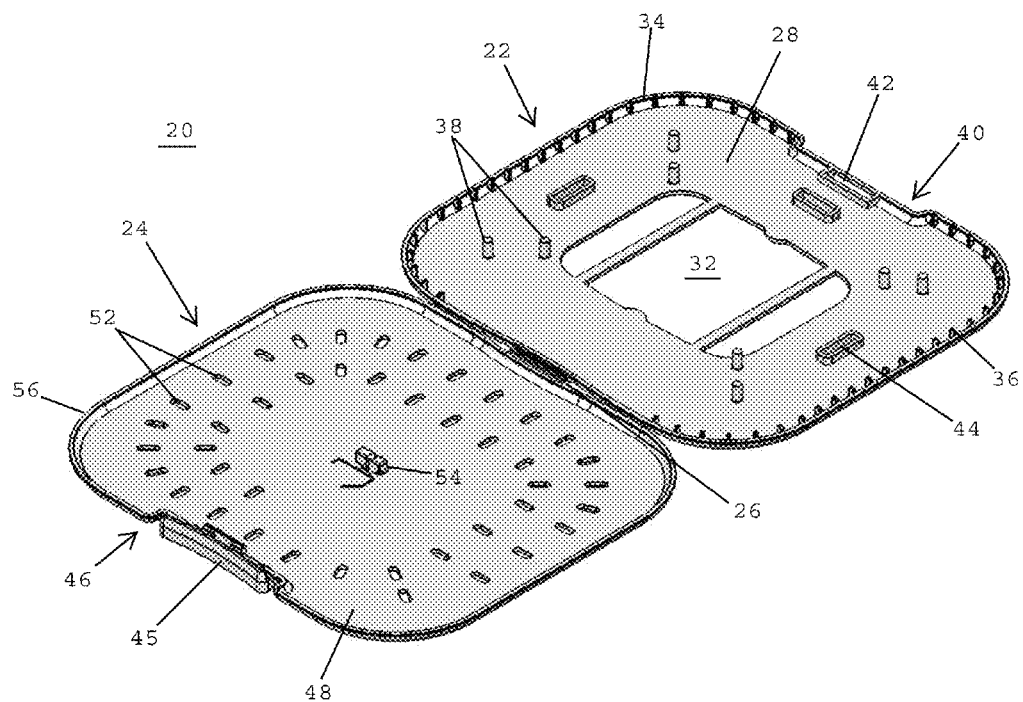
FIG. 1A shows a perspective view of a suture package used for storing, shipping, and dispensing a surgical suture, in accordance with one embodiment of the present invention.
Figure 1B:
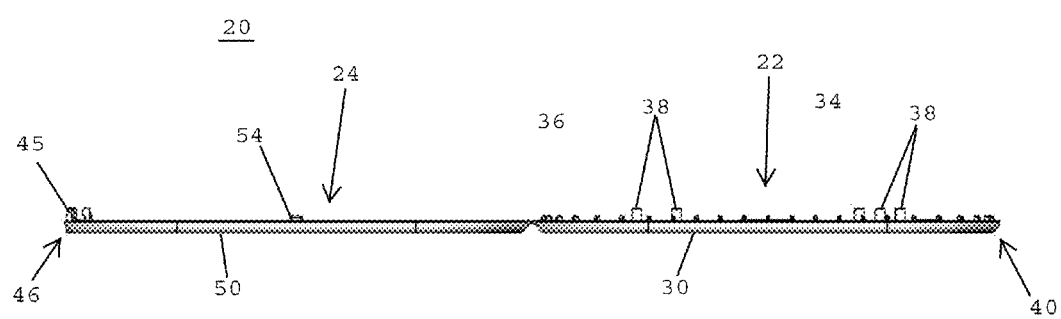
FIG. 1B shows side elevational view of the suture package shown in FIG. 1A.

Referring to FIGS. 1A and 1B, in one embodiment, a suture package 20 used for storing, shipping, and dispensing surgical sutures preferably includes a lid 22 and a base 24. In one embodiment, one or more sutures may be positioned on the base 24 and the lid 22 may be moved over the base for closing the suture package 20. In one embodiment, the lid 22 and the base 24 are desirable coupled together by a hinge 26 that enables the lid 22 to be pivoted over the top of the base 24 for selectively opening and closing the suture package 20.

In one embodiment, the lid 22 preferably has an inner surface 28, an outer surface 30, and a central opening 32 that extends between the inner and outer surfaces 28, 30. The lid 22 preferably has an outer perimeter and an outer ridge 34 that extends around the outer perimeter. The outer ridge 34 desirably projects above the inner surface 28 of the lid 22. The lid 22 preferably includes support flanges 36 that project from the inner surface 28 of the lid and that are coupled with the outer ridge 34 for enhancing the strength of the outer ridge 34 and the structural integrity of the suture package 20.

In one embodiment, the lid 22 preferably includes a plurality of suture retaining posts 38 that project from the inner surface 28 of the lid. The suture retaining posts may include a plurality of posts that are spaced from one another over the inner surface of the lid. In one embodiment, the suture retaining posts 38 are injection-molded posts that are integrally formed with the lid 22. In one embodiment, the suture retaining posts 38 cooperate with the base 24 of the suture package 20 to define at least one "track" that is adapted to hold a suture in place after a suture is wound onto the base and the package has been closed. In one embodiment, the lid 22 includes a set of clips 44A-44C, accessible at the inner surface 28 of the lid, that are adapted to hold a sanitary liner in place for covering the central opening 32.

In one embodiment, an outer edge 40 of the lid 22 includes an opening 42 that extends between the inner and outer surfaces 28, 30 thereof. The opening 42 is preferably adapted to selectively engage a securing element 45 located at an outer edge 46 of the base 24 for holding the lid 22 and the base 24 in a closed position. In one embodiment, the securing element 45 may be engaged for decoupling the securing element 45 from the lid opening 42 for opening the suture package to expose the suture wound on the base 24.

In one embodiment, the base 24 of the suture package preferably includes an inner surface 48 and an outer surface 50. The base 24 preferably includes a plurality of opening 52 extending between the inner and outer surfaces 48, 50. The plurality of openings 52 may form a pattern such as a rectangular or square matrix, a circular pattern or an X-shaped pattern. In one embodiment, at least some of the openings 52 in the base 24 is adapted to receive suture winding posts so that a suture may be wound around the winding posts for positioning the suture on the base. In one embodiment, not all of the openings 52 are filled with a winding post. Rather, only some of the openings 52 are filled and the pattern of the openings that are filled is responsive to a desired winding pattern for a suture. In one embodiment, the openings 52 in the base are elongated so that the openings 52 have a greater length than width. In another embodiment, however, the openings 52 may be circular, with each opening having a common radius and/or shape. In one embodiment, some of the openings may be elongated and some of the openings may be circular.

Referring to FIG. 1A, in one embodiment, the inner surface 48 of the base 24 preferably includes a needle park 54 adapted to secure a suture needle to the base. In one embodiment, the needle park 54 is desirably centrally located over the inner surface 48 of the base 24. In one embodiment, the suture needle secured to the needle park 54 may be secured to an end of a suture.

In one embodiment, the base 24 preferably has an outer perimeter with an outer ridge 56 projecting above the inner surface 48 of the base and extending around the outer perimeter of the base. In one embodiment, when the lid 22 and the base 24 are closed, the outer ridge 34 of the lid 22 preferably engages the outer ridge 56 of the base 24 for forming a connection around the outer perimeter of the suture package 20. In one embodiment, the vertical supports 36 located adjacent the outer perimeter of the lid 22 preferably engage an inner surface of the outer ridge 56 of the base 24 for providing additional structural support to the outer perimeter of the package, thereby enhancing the strength and structural integrity of a closed suture package 20.

In one embodiment, the central opening 32 of the lid 22 may provide access to the inside of the suture package 20 when the suture package is closed. In one embodiment, the central opening 32 is preferably adapted to receive a sanitary liner such as a Triclosan patch (not shown) that prevents contaminants from entering the suture package. The Triclosan patch may be held in place by the set of clips 44A-44C projecting from the inner surface 28 of the lid 22 for holding the Triclosan patch in place prior to using the package.

Figure 2A:
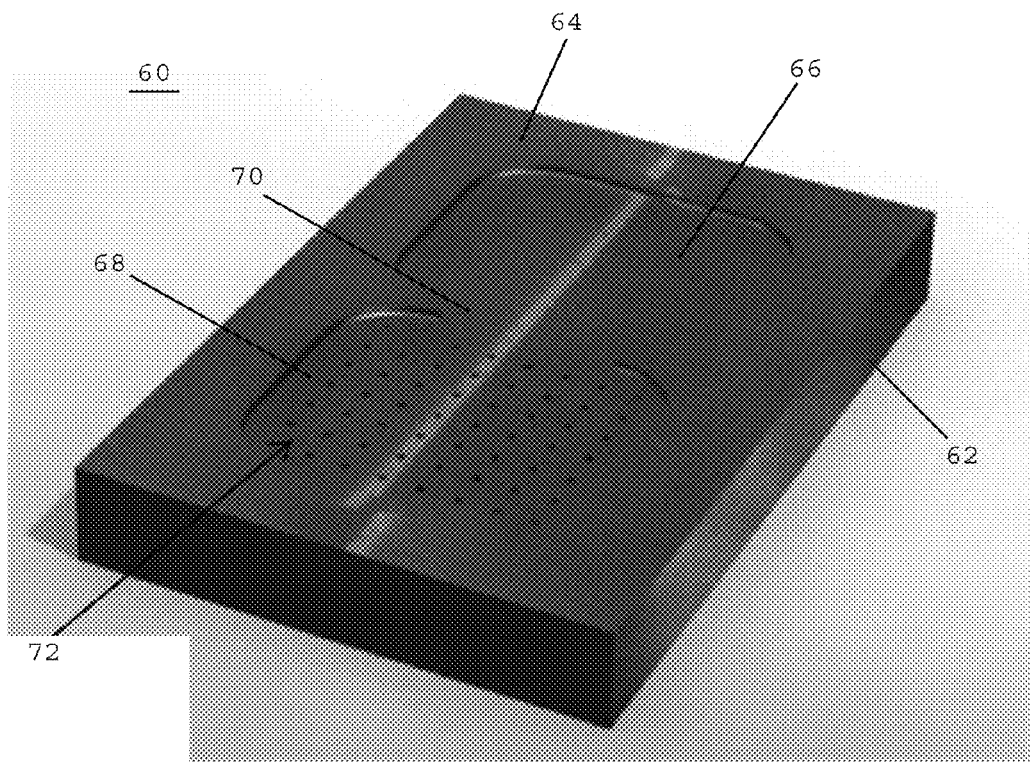
FIGS. 2A-2H show a method of positioning a surgical suture inside a suture package, in accordance with one embodiment of the present invention.

Referring to FIG. 2A, in one embodiment, a fixture 60 is preferably used for positioning at least one suture inside a suture package. The fixture 60 desirably includes a fixture base 62 having a top surface 64. In one embodiment, the top surface 64 preferably has a first depression 66 adapted to receive a lid of a suture package and a second depression 68 adapted to receive a base of a suture package. In one embodiment, the first depression 66 preferably has a size and shape that substantially conforms to the shape of a lid of a suture package, and the second depression preferably has a size and shape that substantially conforms to the shape of the base of a suture package for aligning and holding the suture package in place atop the fixture 60.

In one embodiment, the top surface 64 of the fixture base 62 also desirably includes a central region 68 that extends between the first depression 66 and the second depression 68. In one embodiment, the central region 68 of the fixture base 62 is desirably adapted to receive a hinge, or similar structure, that couples a lid and a base of a suture package together. In one embodiment, the lid and the base are not permanently coupled together so that the top surface of the fixture base 62 does not require a central region formed therein for accommodating a hinge, connector, or similar structure.

In one embodiment, the second depression 68 formed in the top surface 66 of the fixture base 62 preferably includes a plurality of openings 72 formed therein. In the particular embodiment shown in FIG. 2A, the plurality of openings 72 define an 8×7 matrix having eight columns and seven rows. Other matrix patterns having different sizes and configurations may also be provided. In one embodiment, each of the plurality of openings 72 is desirably adapted to have a suture winding post inserted therein. As will be described in further detail herein, a suture may be disposed on the base 24 of the suture package by winding the suture around the suture winding pins. In one embodiment, the fixture 60 is preferably coupled with a vacuum and the plurality of openings 72 enable a vacuum force to be drawn through the base openings of the package for holding a suture in place atop the inner surface of the base. In one embodiment, the vacuum may be drawn until the configuration or shape of the suture wound on the base of the package has been set in place, such as by using heat.

Figure 2B:
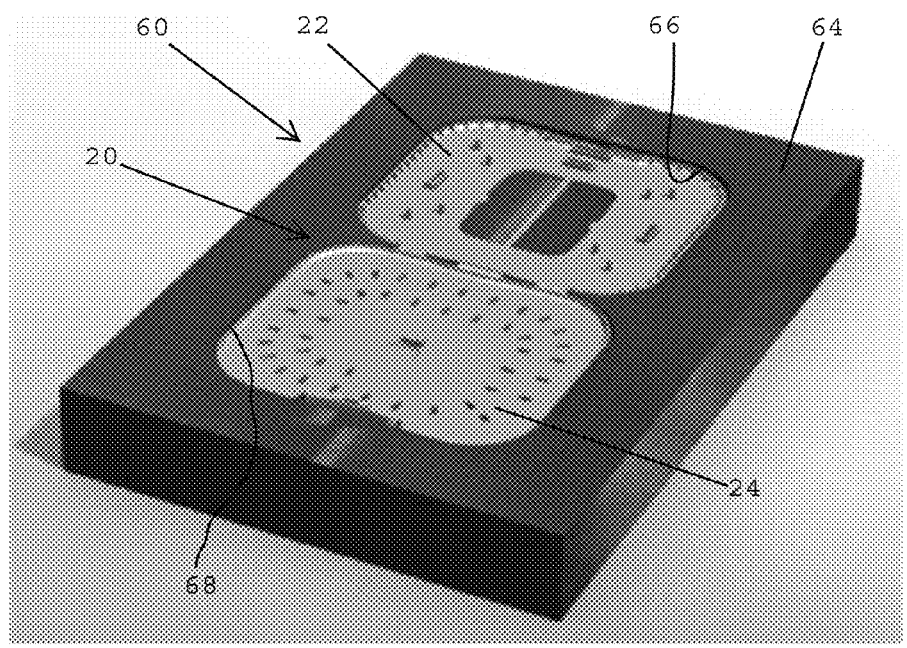

Referring to FIG. 2B, in one embodiment, the suture package 20 is desirably positioned atop the fixture 60 so that the lid 22 is disposed in the first depression 66 and the base 24 is disposed in the second depression 68. In one embodiment, the outer perimeter of the lid 22 desirably closely conforms to the shape of the first depression 66 and the outer perimeter of the base 24 desirably closely conforms to the shape of the second depression 68 for aligning and securing the suture package 20 atop the top surface 64 of the fixture 60.

Figure 2C:
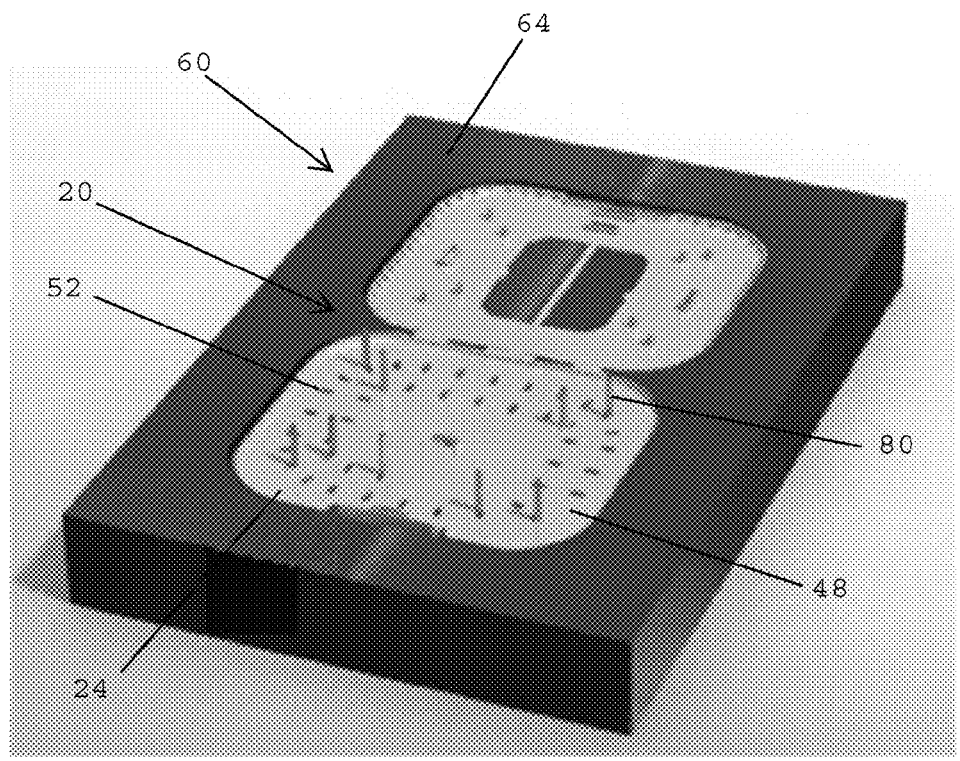

Referring to FIG. 2C, in one embodiment, after the suture package 20 has been aligned over the top surface 64 of the base 62, the plurality of openings 52 in the base 24 are preferably aligned with the plurality of openings 72 formed in the second depression 68. Depending upon the particular winding pattern that is desired for a suture, one or more winding posts 80 are passed through the base openings 52 and inserted into the fixture openings 72 (FIG. 2A). In one embodiment, the inserted winding posts 80 are preferably elongated and have upper ends that project above the inner surface 48 of the base 24.

Figure 2D:
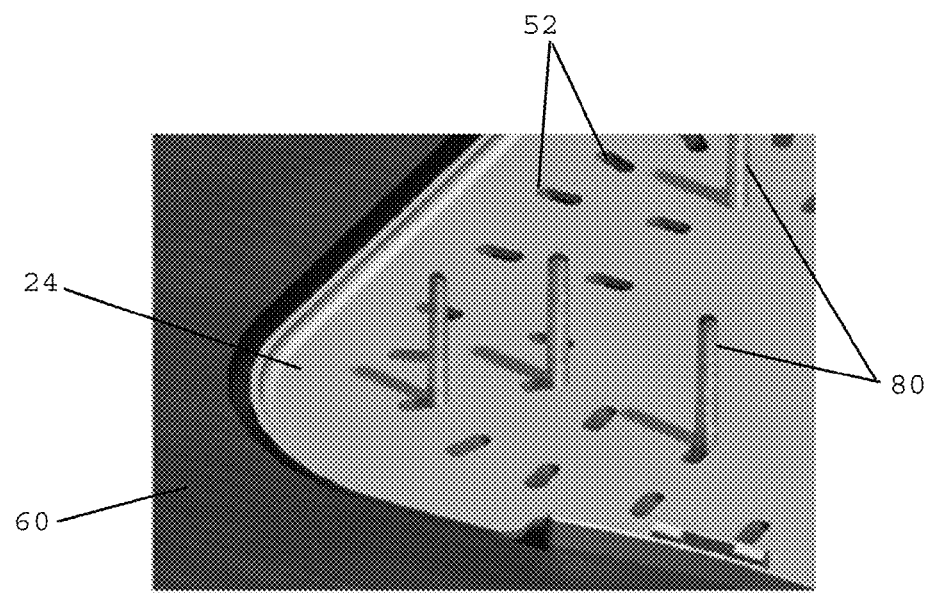

Referring to FIG. 2D, in one embodiment, the winding posts 80 preferably pass through the base openings 52 and hold the base 24 within the second depression 68 of the fixture 60. The winding posts 80 desirably perform various functions including aligning the base openings 52 over the fixture openings 72, and establishing a winding pattern for one or more sutures to be wound on the base.

Figure 2E:
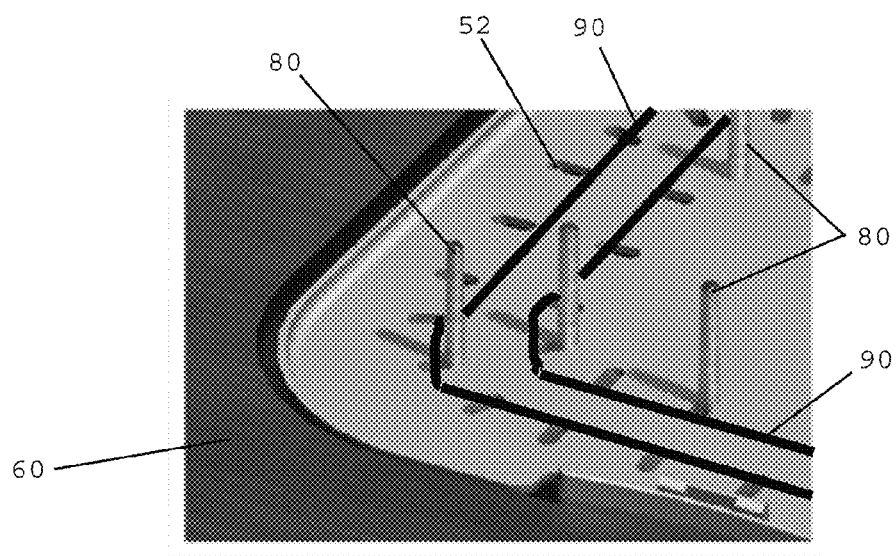

Referring to FIG. 2E, in one embodiment, the winding posts 80 preferably establish and guide the pattern of a suture 90 wound onto the base 24. As the suture 90 is wound around the winding posts 80, vacuum may be drawn through the fixture openings 72 and the base openings 52 for holding the suture 90 in place.

Figure 2F:
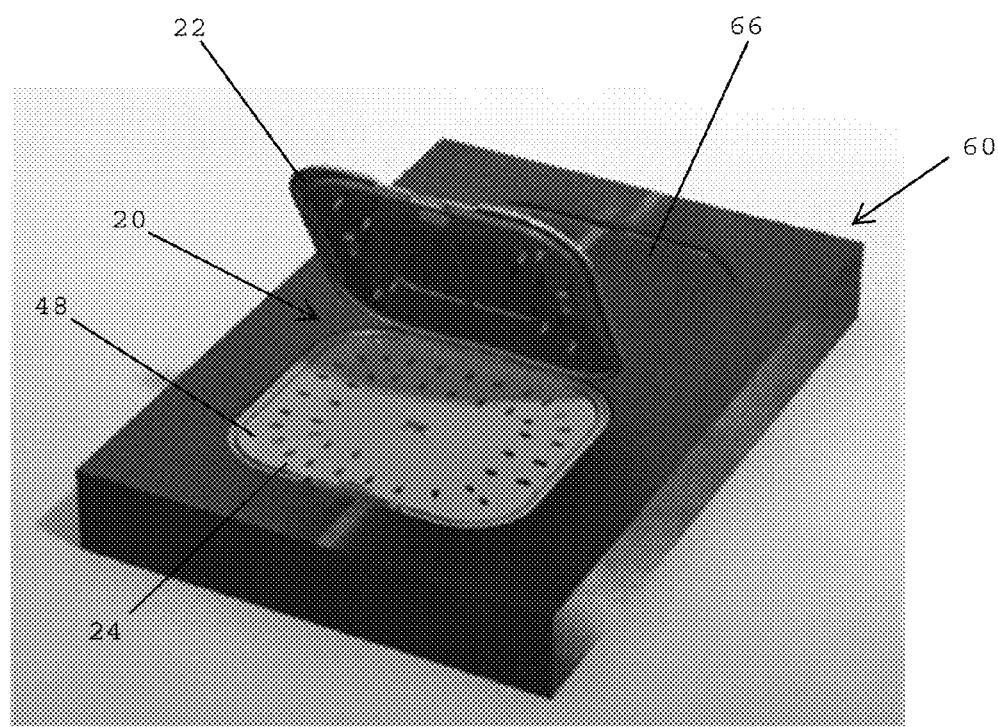

Referring to FIG. 2F, in one embodiment, after the suture material 90 (FIG. 2E) has been wound around the winding posts so that it is positioned over the inner surface 48 of the base 24, the winding posts may be removed from the fixture 60. After the winding posts have been removed, the lid 22 may be lifted from the first depression 66 of the fixture 60 and rotated over the base 24 for closing the suture package 20. In one embodiment, the lid may be closed with the winding posts still in place in the base openings, as the base is lifted from engagement with the winding posts.

Figure 2G:
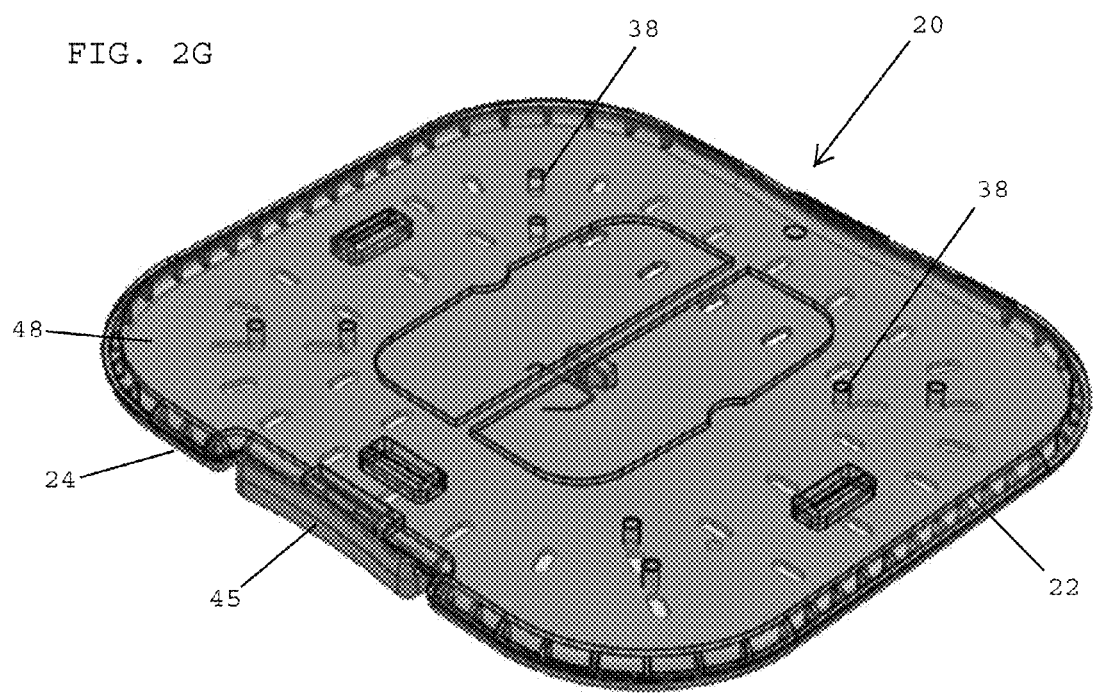

Referring to FIG. 2G, in one embodiment, when the suture package 20 is closed, the lid 22 is snap-fit to the base 24 using the securing element 45. When the lid 22 has been closed atop the base 24, lower ends of the suture retaining posts 38 preferably directly engage the inner surface 48 of the base 24 so that there are no gaps between the lower ends of the suture retaining posts 38 and the inner surface of the base. As a result, when the package is closed, a suture loaded atop the base of a suture package is restrained from moving beyond the suture retaining posts so as to be held in place by the suture retaining posts. In one embodiment, the suture retaining posts 38 preferably define at least one "track" that extends between the lid and the base of the suture package 20. The "track" may have various patterns or shapes such as oval, circular, square, rectangular, figure-eight, etc.

Figures 1, 2G:
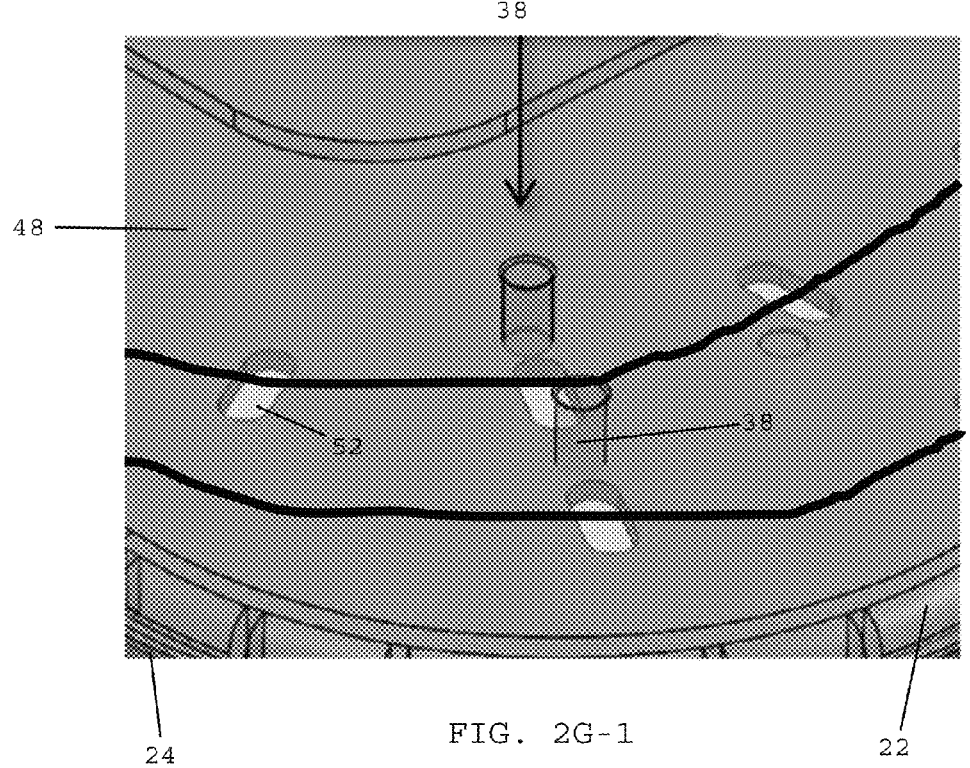

Referring to FIG. 2G-1, in one embodiment, when the package is closed, the suture retaining posts 38 are desirably offset from the base openings 52 so that the posts 38 are not in direct alignment with the base openings 52. In one embodiment, the suture material 90 preferably passes between adjacent suture retaining posts 38, and within the "tracks" defined by the posts 38, for holding the suture material 90 in place during shipment of the package to a surgical site.

Figure 2H:
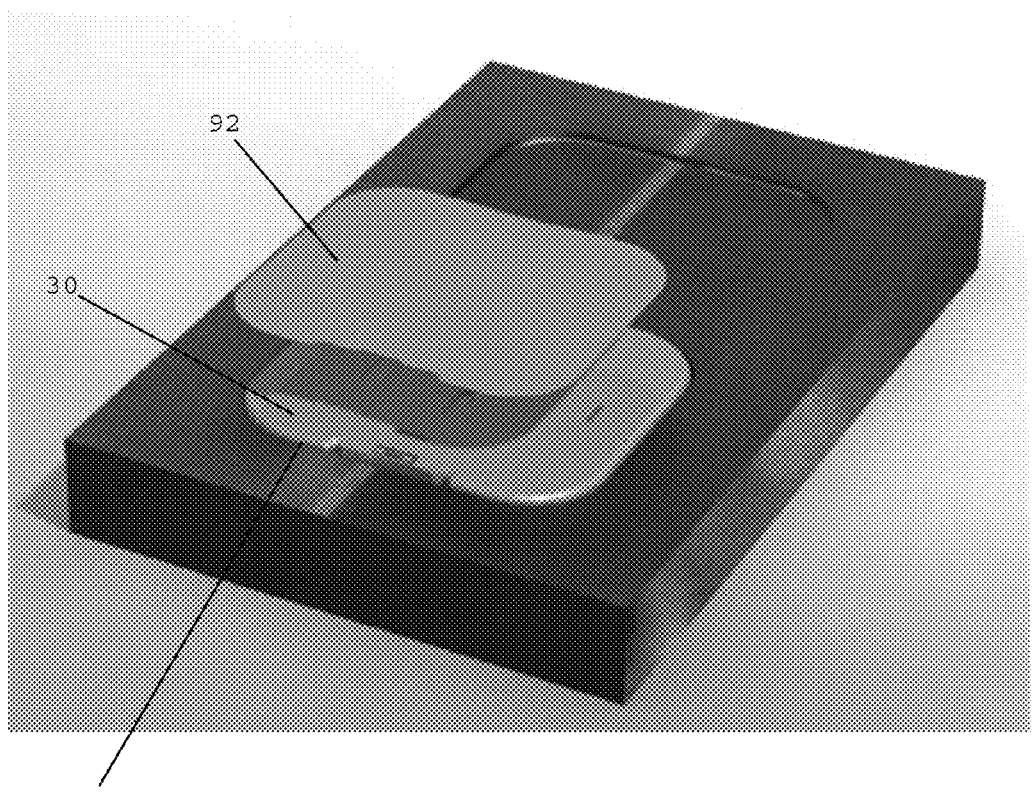

Referring to FIG. 2H, in one embodiment, a liner 92 may be placed over the outer surface 30 of the lid 22 to cover the central opening 32 (FIG. 1A) in the lid. In one embodiment, the liner 92 preferably prevents contaminants from entering the suture package between the time the suture package is manufactured and the time the suture package is used. In one embodiment, the suture package 20 shown in FIG. 2H may be removed from the fixture, placed inside a sterile package for storage, and shipped to a surgical site.

Figure 3A:
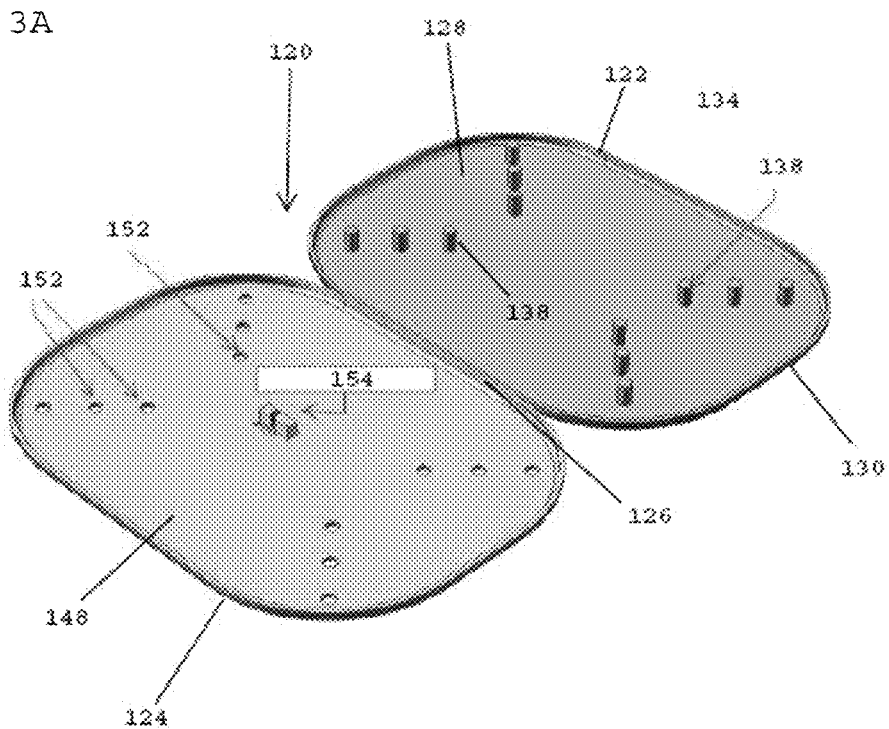
FIGS. 3A-3G show a suture package used for storing, shipping, and dispensing a surgical suture, in accordance with one embodiment of the present invention.
Figure 3B:
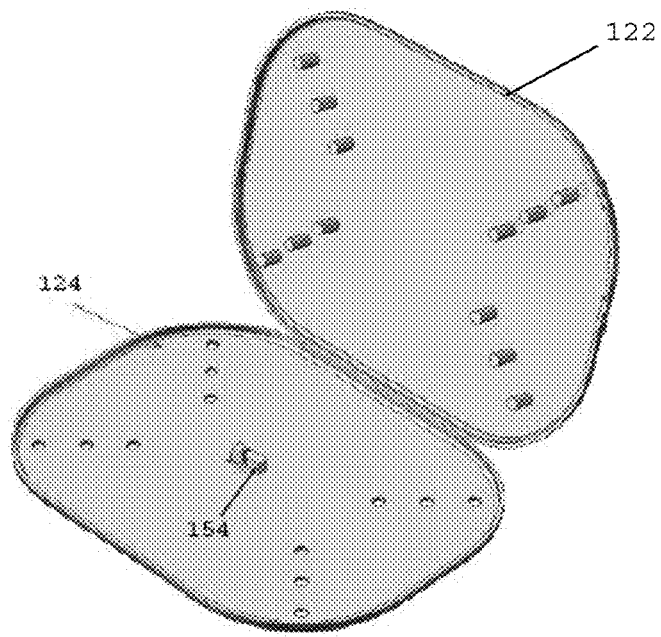
Figure 3C:
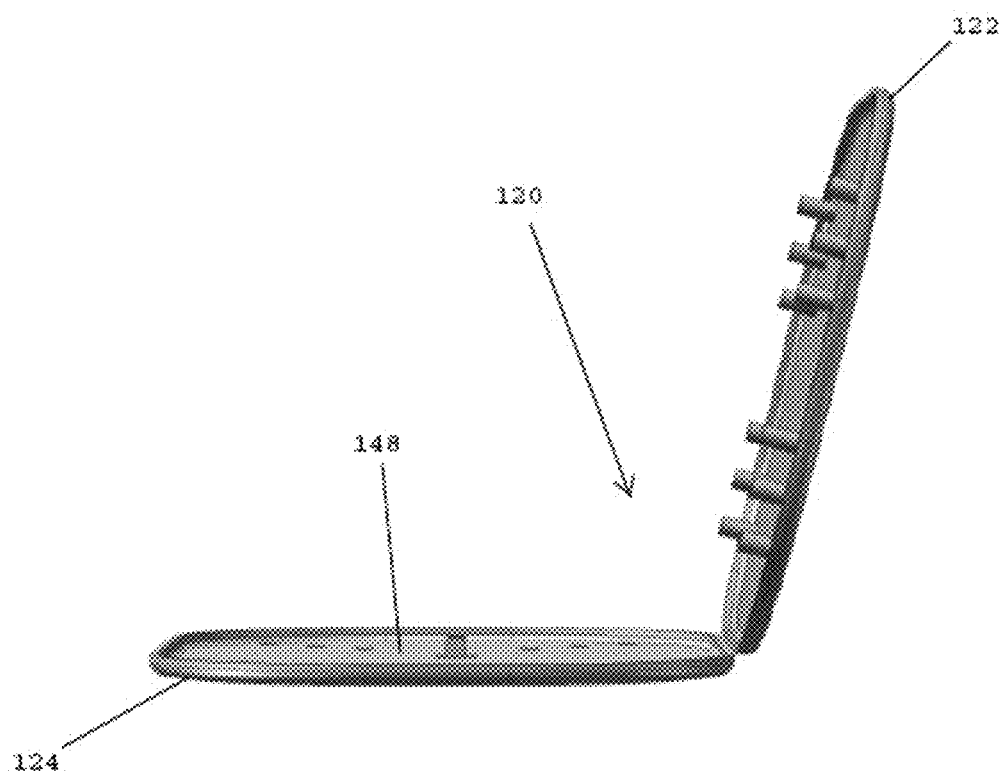

Referring to FIGS. 3A-3C, in one embodiment, a suture package 120 preferably includes a lid 122 and a base 124. In one embodiment, the lid 122 and the base 124 are desirably coupled to one another via a hinge 126 or a connector. The lid 122 desirably includes an inner surface 128, an outer surface 130, and an outer perimeter 134 that is bounded by an outer ridge 136. In one embodiment, the outer ridge 136 preferably projects upwardly from the inner surface 128 of the lid 122. The lid 122 desirably includes one or more suture retaining posts 138 that project away from the inner surface 128 thereof. The suture retaining posts 138 desirably have distal ends that are spaced from the inner surface 128 of the lid 122.

The suture package 120 also desirably includes a base 124 having a plurality of openings 152 formed therein. When the lid 122 is closed atop the base 124, the suture retaining posts 138 are preferably slightly offset from and not in direct alignment with the base openings 152. In one embodiment, when the lid 122 is closed over the base 124, distal ends of the suture retaining posts 138 desirably engage the inner surface 148 of the base 124 so that no gaps are present between the retaining posts 138 and the inner surface 148 of the base 124.

In one embodiment, the base 124 preferably includes a needle park 154 for securing a suture needle coupled to an end of a suture. The needle park 154 is desirably integrally formed with the base 124 and is accessible at the inner surface 148 of the base 124. FIGS. 3B and 3C show the suture package 120 with the lid 122 partially closed over the inner surface 148 of the base 124.

Figure 3D:
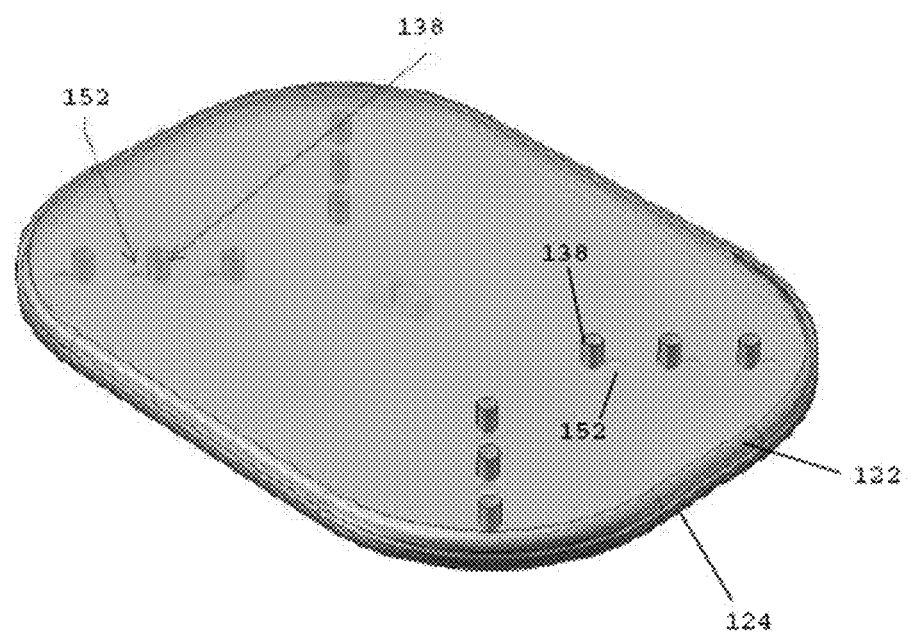

Referring to FIG. 3D, in one embodiment, when the lid 22 is fully closed over the base 24, the suture retaining posts 138 are offset from the base openings 152. In one embodiment, the suture retaining posts 138 define at least one "track" that extends between the lid and the base. The track formed by the suture retaining posts 138 desirably holds suture material 90 in place during shipment and storage of the suture package 120, or as long as the package remains closed.

Figure 3E:
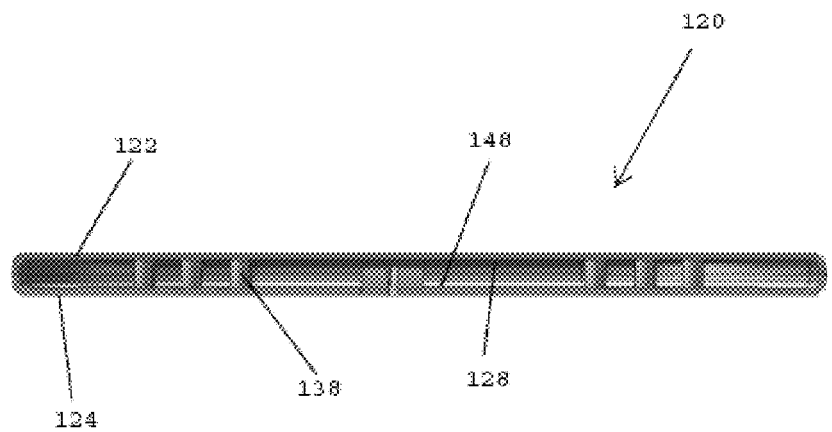

Referring to FIG. 3E, in one embodiment, when the suture package 20 is closed, the suture retaining posts 138 preferably extend from the inner surface 128 of the lid 122 to the inner surface 148 of the base 124. As noted above, the suture retaining posts 138 desirably hold suture material stored within the suture package in place between adjacent sets of suture retaining posts 138.

Figure 3F:
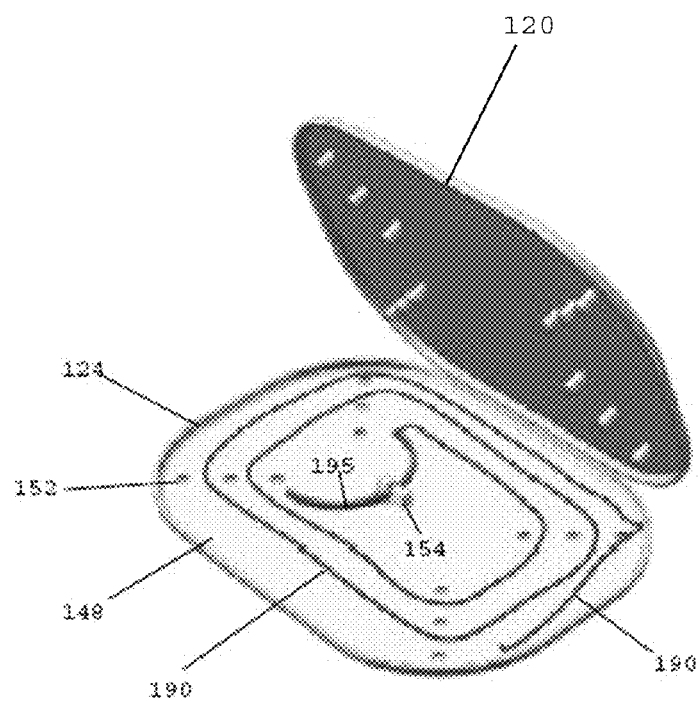

FIG. 3F shows a suture 190 positioned over the inner surface 148 of the base 124, after the base 124 has been decoupled from a fixture having winding posts, such as the fixture shown and described above in FIGS. 2A-2H. After the suture winding posts have been removed from the base openings 152, the suture material 190 is preferably offset from and passes by the base openings 152. A suture needle 195 that is attached to an end of the suture material 190 is desirably secured to the needle park 154 atop the inner surface 148 of the base 124.

Figure 3G:
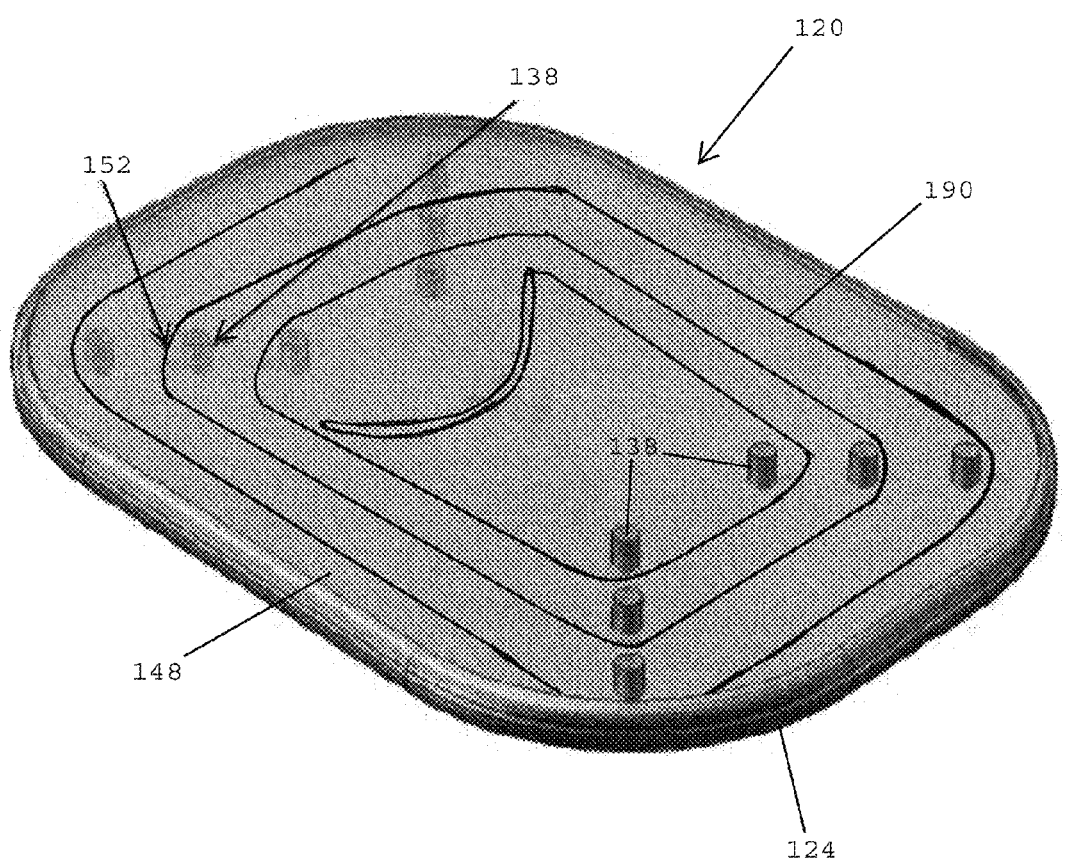

Referring to FIG. 3G, in one embodiment, when the package 124 is closed, the suture retaining posts 138 engage the inner surface 148 of the base 124. The lower ends of the suture retaining posts 138 engaging the inner surface 148 of the base 124 are preferably disposed adjacent to and offset from the plurality of base openings 152 associated therewith. The suture 190 positioned atop the inner surface of the base 124 preferably extends between adjacent ones of the suture retaining posts 138. When the package 120 is closed, the suture retaining posts 138 define at least one "track" in which the surgical suture 190 is wound over the inner surface of the base. As long as the suture package remains closed, the one or more "tracks" defined by the engagement of the suture retaining posts with the inner surface of the base prevents the shifting of the suture 190 positioned over the inner surface of the base. When the lid 120 is opened, as shown in FIG. 3F, the suture retaining posts 138 on the lid 120 are pulled away from the inner surface 148 of the base 124 to provide for unconstrained removal of the suture 190 from the base 124.

Figure 4:
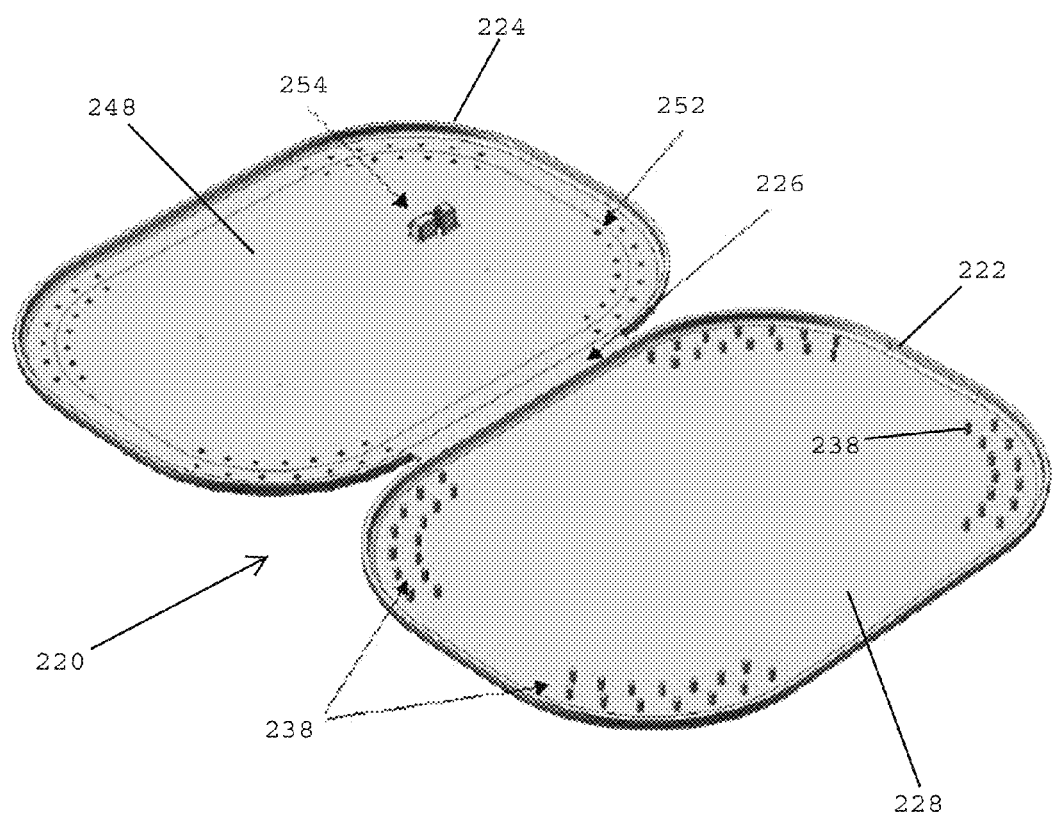
FIG. 4 shows a suture package used for storing, shipping, and dispensing a surgical suture, in accordance another embodiment of the present invention.

Referring to FIG. 4, in one embodiment, a suture package 220 preferably includes a lid 222, a base 224 and a hinge 226 that couples the lid and the base together. The base 224 preferably includes a plurality of base openings 252 defining an oval pattern extending adjacent the outer perimeter of the base. The lid 222 preferably includes an inner surface 228 and a plurality of suture retaining posts 238 projecting from the inner surface 228. The plurality of retaining posts 238 desirably define at least one oval shaped "track" that extends adjacent the outer perimeter of the lid 222. After a fixture having winding posts (FIG. 2C) has been used for winding suture material over the inner surface of the base 224, the lid 222 may be closed atop the base 224. The suture retaining posts 238 of the lid 222 are preferably slightly offset, adjacent and not in alignment with the base openings 252. As a result, the suture retaining posts 238 preferably project from the inner surface 228 of the lid 222 and have distal ends that contact the inner surface 248 of the base 224 so as to define one or more "tracks" that hold the wound suture material in place during shipment and storage of the package.

Although the present invention is not limited by any particular theory of operation, it is believed that the various suture packages disclosed herein provide for unconstrained removal of a suture from a package. As described above, prior art suture packages include flanges, projections or corners that may catch a suture or an appendage on a suture as it is removed from the package. These drawbacks are avoided when using the suture packages disclosed herein because when the lid is opened, the suture retaining structure in the package (i.e. the suture retaining posts) are pulled away from the base so that there is no structure that may constrain removal of the suture from the base. The retaining posts on the lid limit and/or constrain movement of the suture only when the lid is closed. However, the suture retaining posts are completely removed away from the suture material when the lid is opened so that unconstrained removal of the suture material may occur. The present invention also enables a single package design to be used for winding suture material having various patterns. For example, the suture package shown in FIGS. 3A-3C may have a first configuration whereby suture material is wound in a figure eight configuration. The package may be modified by re-arranging the position of the winding posts, so that the suture material is wound in an oval pattern. Further modifications may be made for providing additional winding patterns.

Referring to FIG. 5, in one embodiment, a suture package 320 preferably includes a lid 322 that is hingedly secured to a base 324 via hinges 326A and 326B. The suture package 320 preferably includes a securing element or latch 345 that is connected to the lid 322 and that is engageable with the base 324 for selectively opening and closing the suture package 320. In one embodiment, the suture package 320 preferably includes a cantilever element 327 that is preferably attached to the lid of the suture package 320. In one embodiment, a gap 329 preferably extends between the cantilever element 327 and the outer ridge 356 of the base 324. In one embodiment, when it is desirable to open the suture package 320 so that the lid moves away from the base 324 for accessing one or more sutures stored therein, the base may be placed atop an operator's palm so that the lid 322 faces away from the operator's palm. The operator may press the latch 345 and the cantilever element 327 toward one another, which desirably opens the lid 322 from the base 324. Although the present invention is not limited by any particular theory of operation, it is believed that providing a cantilever element 327 attached to the lid 322, with a gap 329 between the cantilever element and the outer ridge 356 of the base 324, facilitates opening of the suture package 320. In addition, it is believed that providing the cantilever element 327 will facilitate springing open the lid 322 relative to the base 324 for more easily accessing the one or more sutures stored therein.

The various embodiments of the present invention show the suture retaining posts projecting from the lid of a suture package. In one embodiment, the suture retaining posts may be provided on the base of a suture package and the plurality of openings may be provided on the lid of a suture package and still fall within the scope of the present invention.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A suture package comprising:
   a base including an outer surface, an inner surface, and a plurality of openings extending between said outer and inner surfaces;
   a lid including an outer surface, an inner surface, and a plurality of posts projecting from said inner surface, wherein said plurality of posts have proximal ends connected with said lid and distal free ends;
   a hinge interconnecting said lid and said base for moving said suture package between an open configuration and a closed configuration;
   wherein when said suture package is in the closed configuration said inner surface of said lid is spaced from and opposes said inner surface of said base with the distal free ends of said posts engaging said inner surface of said base at locations that are offset from and adjacent said plurality of openings extending through said base; and
   at least one suture overlying said inner surface of said base, wherein when said suture package is moved from the closed configuration to the open configuration said plurality of posts are pulled away from the inner surface of said base and said at least one suture overlying said inner surface of said base so that said at least one suture may be removed from said base.

2. The suture package as claimed in claim 1, wherein said base includes a needle park adapted for securing a suture needle to said base of said suture package.

3. The suture package as claimed in claim 1, wherein when said package is in the closed configuration said posts span the entire length of the space between said opposing inner surfaces of said base and said lid.

4. The suture package as claimed in claim 3, wherein said base includes an outer ridge projecting from said inner surface of said base, and said lid includes an outer ridge projecting from said inner surface of said lid that is adapted to engage said outer ridge of said base when said suture package is closed.

5. The suture package as claimed in claim 4, wherein said outer ridge of said base defines an outer perimeter of said base, and said outer ridge of said lid defines an outer perimeter of said lid.

6. The suture package as claimed in claim 1, wherein said hinge interconnects opposing trailing edges of said lid and said base, and said suture package further comprises a clasp engageable with at least one of said lid and said base for holding said suture package in the closed configuration.

7. The suture package as claimed in claim 3, wherein said plurality of posts are integrally formed with said lid.

8. The suture package as claimed in claim 3, wherein when said suture package is in the closed configuration said plurality of posts define at least one track between adjacent ones of said posts and said at least one suture extends within the at least one track between the adjacent ones of said posts.

9. The suture package as claimed in claim 3, wherein each of said plurality of posts projecting from said inner surface of said lid has a length that spans a gap extending between said inner surface of said lid and said inner surface of said base when said suture package is in the closed configuration.

10. The suture package as claimed in claim 3, wherein said plurality of posts projecting from said inner surface of said lid define at least one suture retaining track extending between said inner surface of said lid and said inner surface of said base.

11. The suture package as claimed in claim 3, wherein said inner surface of said base comprises a plurality of recesses adjacent said plurality of openings in said base adapted to seat the distal free ends of said plurality of posts projecting from said inner surface of said lid.

12. The suture package as claimed in claim 3, wherein said lid and said base comprise polymer materials.

13. The suture package as claimed in claim 3, wherein when said suture package is in the closed configuration, said lid posts engage said inner surface of said base for defining at least one suture retaining track over said inner surface of said base for constraining said at least one suture between adjacent ones of said lid posts.

14. A suture package comprising:
    a base including an outer surface; an inner surface, and a plurality of openings extending between said outer and inner surfaces;
    a lid including an outer surface, an inner surface, and a plurality of suture retaining posts projecting from said inner surface, each said suture retaining post having a proximal end connected with said lid and a distal free end that is not connected with said base;
    a hinge interconnecting said lid and said base for moving said suture package between an open configuration in which the distal free ends of said suture retaining posts are spaced from said inner surface of said base and a closed configuration in which said inner surface of said lid is spaced from and opposes said inner surface of said base with the distal free ends of said suture retaining posts engaging said inner surface of said base at locations that are offset from and adjacent said plurality of openings extending through said base; and
    at least one suture overlying said inner surface of said base, wherein as said suture package is moved from the closed configuration to the open configuration said plurality of posts are pulled away from the inner surface of said base and said at least one suture overlying said inner surface of said base so that said at least one suture may be removed from said base.

15. The suture package as claimed in claim 14, wherein said base includes an outer ridge projecting from said inner surface of said base for defining a concave shaped base, and said lid includes an outer ridge projecting from said inner surface of said lid for defining a concave shaped lid, and wherein said outer ridge of said lid is adapted to engage said outer ridge of said base when said suture package is in the closed configuration.

16. The suture package as claimed in claim 14, wherein said lid and said base comprise polymers.

17. The suture package as claimed in claim 14, wherein said suture retaining posts are integrally formed with said lid of said suture package, and wherein when said package is in the closed configuration each said post has a length that spans the entire gap between said spaced inner surfaces of said lid and said base.

* * * * *